United States Patent [19]

Bagli et al.

[11] Patent Number: 4,617,393

[45] Date of Patent: Oct. 14, 1986

[54] 5-SUBSTITUTED-6-AMINOPYRIMIDINES, COMPOSITION AND USES AS CARDIOTONIC AGENTS FOR INCREASING CARDIAC CONTRACTILITY

[75] Inventors: Jehan F. Bagli, Princeton, N.J.; Steven M. Peseckis, Levittown, Pa.

[73] Assignee: American Home Products Corporation, New York, N.Y.

[21] Appl. No.: 757,214

[22] Filed: Jul. 19, 1985

[51] Int. Cl.$^4$ .................. C07D 239/02; A61K 31/505
[52] U.S. Cl. .................................... 544/319; 544/321; 514/269
[58] Field of Search ................. 544/319, 321; 514/269

[56] References Cited

U.S. PATENT DOCUMENTS

| | | | |
|---|---|---|---|
| 3,673,184 | 6/1972 | Minami et al. | 544/122 |
| 3,908,012 | 9/1975 | De Angelis et al. | 514/269 |
| 3,950,525 | 4/1976 | De Angelis et al. | 514/269 |
| 4,072,746 | 2/1978 | Lesher et al. | 514/334 |
| 4,313,951 | 2/1982 | Lesher et al. | 514/334 |
| 4,507,304 | 3/1985 | Bagli | 514/269 |
| 4,595,910 | 3/1985 | Bagli | 514/26 |

FOREIGN PATENT DOCUMENTS 126711  11/1984  European Pat. Off. .
130735  9/1985  European Pat. Off. .

OTHER PUBLICATIONS

Kobayashi et al., Chem. Abst, 75-49129m, eq. JP '698.
Rogge et al, Chem. Abst., 81-25691m, eq. German (East) 101894.
Durant et al, Chem. Abst., 82-73036u, eq. U.S. 4,470,985.
Meyer et al., Chem Abst., 102-132065j, eq. EP '711.
Hoegerle et al, Chem. Abst., 99-175787h, eq. U.S. '375.
Bagli, Chem. Abst., 103-6358q, eq. EP '735.
Mochida Pharm KK, Derwent Farmdoc, 27363, eq. JP 110708.
Byk Gulden Lomberg, Derwent Farmdoc, 62457w, eq. DT 2410650.
Fujisawa Pharm. KK, Derwent Farmdoc, 05783j, eq. JP 7176981.
Byk Gulden Lomberg, Derwent Farmdoc, 10368u, eq. NL-7210637.
Derwent Farmdoc., 31812R, eq. UK 1189188.
A. Kumar et al, Synthesis (9) 748 (1980).
Derwent Abst., DE-72790, 5-5-70.

*Primary Examiner*—Donald G. Daus
*Assistant Examiner*—Cecilia Shen
*Attorney, Agent, or Firm*—Walter Patton

[57] ABSTRACT

Herein is disclosed amino-pyrimidine derivatives, therapeutically acceptable acid addition salts thereof, processes for their preparation, methods of using the derivatives and pharmaceutical compositions. The derivatives are useful for increasing cardiac contractility in a mammal.

23 Claims, No Drawings

5-SUBSTITUTED-6-AMINOPYRIMIDINES, COMPOSITION AND USES AS CARDIOTONIC AGENTS FOR INCREASING CARDIAC CONTRACTILITY

BACKGROUND OF THE INVENTION

This invention relates to novel amino-pyrimidine derivatives, to therapeutically acceptable addition salts thereof, to processes for their preparation, to methods of using the derivatives and to pharmaceutical compositions of the derivatives. These derivatives are useful as cardiotonic agents for increasing cardiac contractility.

Although the amino-pyrimidine derivatives of this invention are novel compounds, a number of pyrimidines and 4-oxopyrimidines are described, for example, J. Bagli, U.S. Pat. No. 4,505,910, Mar. 19, 1985, J. Bagli, U.S. Pat. No. 4,507,304, Mar. 26, 1985, B. Rogge et al., Chem. Abstr. 81, 25691m (1974) for East German Patent No. 101,894, Nov. 20, 1973; S. Kisaki et al., Chem. Pharm. Bull., 22, 2246 (1974); Derwent Publications Ltd., Farmodoc 62457W for German Offenlegenshift No. 2,410,650, published Sept. 11, 1975; Derwent Publications Ltd., Farmdoc 05783J for Japanese Patent No. 7,176,981, published Oct. 10, 1982; Derwent Publications Ltd., Farmdoc 10368U for Netherland Patent No. 7,210,637, published Feb. 6, 1973; Chemical Abstracts, 75, 49129m (1971) for Japanese Patent No. 7,108,698, published Mar. 5, 1971; A. Kumar et al., Synthesis, (9), 748 (1980); Derwent Publications Ltd., Farmodoc 46076R for East German Patent No. 72,790, published May 5, 1970; and Derwent Publications Ltd., Farmodoc 31812R for British Patent No. 1,189,188, published Nov. 9, 1966. The pyrimidines described in the above reports are distinguished from the compounds of this invention by the different substituents on the pyrimidine ring and the reported biological activity. The amino-pyrimidine derivatives of this invention are also distinguished from the cardiotonic pyridinones, exemplified by G. Y. Lesher et al., U.S. Pat. No. 4,072,746, Feb. 7, 1978 and G. Y. Lesher et al., U.S. Pat. No. 4,313,951, Feb. 2, 1982, by having different rings and different substitution on the rings.

SUMMARY OF THE INVENTION

The compounds of this invention are represented by formula I

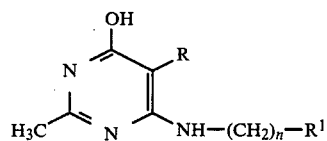

wherein R is halogen or lower alkyl containing 1 to 3 carbon atoms; $R^1$ is hydrogen, hydroxy, cyclopropyl; pyridinyl, 1-methyl-1H-pyrrol-2-yl, 2-furanyl, phenyl; and n is an integer from 1 to 3, and the pharmaceutically acceptable addition salts thereof.

A preferred group of compounds of this invention is represented by formula I wherein R is halogen, methyl, isopropyl, $R^1$ is hydrogen, hydroxy, cyclopropyl, 3- and 4-pyridinyl, 1-methyl-1H-pyrrol-2-yl, 2-furanyl and phenyl, and n is an integer from 1 to 3, and the pharmaceutically acceptable addition salts thereof.

The structural formula of the compounds of the present invention are represented by the enol form in formula (I). They may equally be represented by the keto form ($I^1$) or ($I^2$)

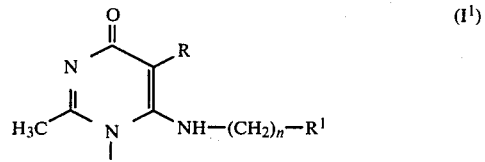

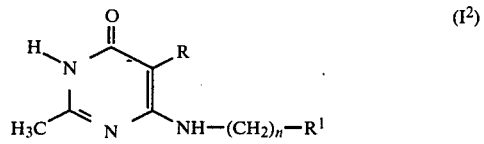

wherein R, $R^1$ and n are as defined herein.

This invention also relates to a pharmaceutical composition comprising a compound of formula I or a therapeutically acceptable addition salt thereof and a pharmaceutically acceptable carrier.

This invention also relates to a method for increasing cardiac contractility in a mammal which comprises administering to the mammal an effective cardiotonic amount of a compound of formula I or a therapeutically acceptable addition salt thereof.

DETAILED DESCRIPTION OF THE INVENTION

The term "lower alkyl" as used herein means straight and branched chain alkyl radicals containing from one to three carbon atoms, and includes methyl, ethyl, propyl, and 1-methylethyl.

The term "inorganic proton acceptor" as used herein means the inorganic bases, preferably the alkali metal hydroxides, alkoxides, carbonates and bicarbonates, for example, sodium hydroxide, potassium hydroxide, sodium carbonate, sodium bicarbonate, potassium carbonate, sodium hydride, sodium methoxide and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the basic compound. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula I are also capable of forming addition salts with sodium or potassium. These salts are prepared by reacting the latter compounds of formula I with one or more equivalents of sodium or potassium, or a strong base of sodium or potassium, for example, sodium hydroxide, potassium t-butoxide, sodium hydride and the like. These salts, like the acid addition salts, when administered to a mammal possess the same pharmacological activities as the corresponding nonsalt compound of formula I.

The compounds of formula I or a therapeutically acceptable addition salt thereof are useful as cardiotonic agents for increasing cardiac contractility in a mammal. The cardiotonic effect is demonstrated in standard pharmacological tests, for example, in causing an increase in the contractile force of the isolated cat papillary muscle and reversal of pentobarbital-induced cardiac failure in the dog.

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example, hard paraffin or cetyl alcohol. These compositions can also contain a sweetening agent, flavoring agent and antioxidant.

The dosage of the compounds of formula I as cardiotonic agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective cardiotonic amount of the compounds for oral administration can usually range from about 0.05 to 50 mg per kilogram body weight per day in single or divided doses although as aforementioned variations will occur. However, a dosage level that is in the range of from about 0.2 to 20 mg per kilogram body weight per day in single or divided doses is employed most desirably for oral administration in order to achieve effective results.

The compounds of formula I also can be used to produce beneficial effects in the treatment of congestive heart failure when combined with a therapeutically effective amount of another agent commonly used in the treatment of congestive heart failure. Such agents include, for example: vasodilators, i.e. isosorbide dinitrate, captopril, nifedipine, hydralazine and prazosin; diuretics, i.e. hydrochlorothiazide, furosemide and spironolactone; and other cardiotonics, i.e. digitalis and dobutamine. A combination of the above agents can be substituted for a single agent. Suitable methods of administration, compositions and dosages of the agents are well known in the art; for instance, "Physican Desk Reference," 37 ed., Medical Economics Co., Oradell, N.J., U.S.A., 1983. When used in combination, the compound of formula I is administered as described previously.

The compounds of formula I are prepared in the following manner.

Reaction scheme 1 illustrates a method for preparing some of the compounds of formula I.

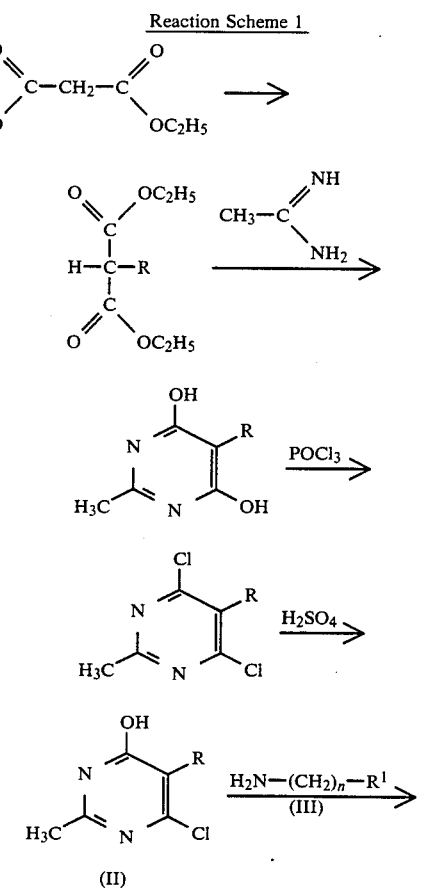

-continued
Reaction Scheme 1

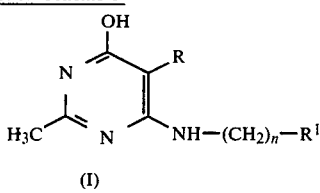

wherein R, $R^1$ and n are as defined herein.

With reference to reaction scheme 1, the pyrimidine of formula (II) in which R is defined herein is reacted with the amine of formula (III) in which $R^1$ and n are as defined herein to give the corresponding compound of formula (I) in which R, $R^1$ and n are as defined herein. About one to five equivalents of the amine of formula (III) are usually used and the reaction is conducted in an inert organic solvent, preferably 1,2-dimethoxyethane, at about 50° to 100° C. for about 10 to 30 hours.

The required pyrimidines of formula (II) wherein R is as defined herein are prepared by treating with aqueous sulfuric acid 2-methyl-4,6-dichloro-5-(substituted)-pyrimidine wherein the 5-substituent is R as defined herein.

The 2-methyl-4,6-dichloro-5 substituted pyrimidine wherein the 5-substituent is R as defined herein is prepared by suspending 2-methyl-4,6-dihydroxy-5-(substituted)pyrimidine in phosphorous oxychloride.

The required pyrimidine of formula II wherein R is bromine is prepared by brominating 2-methyl-4-hydroxy-6-chloropyrimidine, which in turn is obtained by treating 2-methyl-4,6-dichloropyrimidine with aqueous sulfuric acid.

EXAMPLE 1

5-Bromo-2-methyl-6-[(3-pyridinylmethyl)amino]-4-pyrimidinol

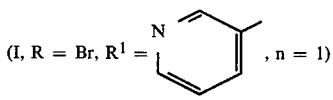

(Step a) Preparation of 2-Methyl-4-hydroxy-6-chloropyrimidine

To a solution of water (8.5 mL) in sulfuric acid (32 mL) was added 2-methyl-4,6-dichloropyrimidine (13.4 g, 82 mmol). The mixture was stirred for 1 hour at 23° C. and then poured onto an ice/water slurry containing sodium hydroxide (24 g, 600 mmol). When the ice had melted, sodium chloride (90 g) was added and allowed to dissolve. The product precipitated and was isolated by filtration (9.5 g) 80%. An analytical sample was prepared by recrystallization from ethanol m.p. 230°-234° C. as a fluffy yellow solid.

$^1$H NMR (60 MHz, DMSO-D$_6$) δ 13.0 (brs, 1H, OH), 6.45 (s, 1H), 2.32 (s, 3H);

IR(Nujol) 2600-3100, 1650, 855 cm$^{-1}$;

UV(MeOH) λ 276.5 (ε 4454), 225.0 (ε 5663);

mass spectrum m/e 144 (M$^+$, 100%), 116 (M$^+$—CO, 53%);

Anal. Calcd. for C$_5$H$_5$ClN$_2$O: C, 41.52; H, 3.46; N, 19.38. Found: C, 41.44, H, 3.55; N, 19.32.

(Step b) Preparation of 2-Methyl-4-hydroxy-5-bromo-6-chloropyrimidine

A stirred solution of 6.15 g (425 mmol) of 2-methyl-4-hydroxy-6-chloropyrimidine in 150 mL of glacial acetic acid and 600 mL of chloroform at 23° C. was treated dropwise with 30.9 mL (96.4 g, 603 mmol, 1.3 equiv.) of bromine. From the nearly homogeneous solution a precipitate rapidly formed. The reaction mixture was stirred for 18 hours at 23° C. and then was concentrated in vacuo following filtration. The combined residue and isolated solid were recrystallized from water to afford, after in vacuo drying, 73.3 g 83%, (353 mmol) of pure product m.p. 248°-249° C. off-white crystals.

$^1$H NMR (200 MHz, DMSO-D$_6$) δ 12.60 (br s, 1H), 2.14 (s, 3H);

IR (KBr) 2700-3100, 1660 (C=O), 1590 (C=C, C=N) cm$^{-1}$;

UV (MeOH) λ 287.0 (ε 6600), 233.5 (ε 4280);

mass spectrum m/e 224 (M$^+$, 100%), 222 (M$^+$, 81%), 196 (M$^+$—CO, 25%), 194 (M$^+$—CO, 18%)

(Step c) Preparation of 5-Bromo-2-methyl-6-[(3-pyridinylmethyl)amino]-4-pyrimidinol A stirred suspension of 5.11 g (24.6 mmol) of 2-methyl-4-hydroxy-5-bromo-6-chloropyrimidine and 7.50 mL (7.97 g, 73.8 mmol, 3 equiv.) of 3-(aminomethyl)pyridine in 15 mL of dimethoxyethane (DME) was heated at 70° C. for 21 hours under a dry atmosphere. The cooled reaction mixture at 23° C. was diluted with 9 mL of water and stirred for 15 minutes. The observed solid precipitate was isolated by filtration (sintered glass funnel), rinsed with diethyl ether (5 mL) and water (5 mL), and recrystallized from methanol (initial 580 mL of hot methanol upon concentration to 280 mL afforded 4.43 g of free base, further reduction of mother liquors to 90 mL afforded 1.10 g free base) to afford a total of 5.54 g (18.8 mmol) of analytically pure free base. From a 30.0 g scale reaction run proportionate to that described above (134 mmol of 2-methyl-4-hydroxy-5-bromo-6-chloropyrimidine) was obtained 40.6 g of crude free base which was recrystallized from 650 mL of 1:1 MeOH:CHCl$_3$ to afford, in three crops, 33.2 g (112 mmol, 84%) of pure free base m.p. 251°-252° C.

To 12.6 g. (42.5 mmol) of free base suspended in 80 mL of MeOH was added 43 mL (86 mmol, 2 equiv.) of methanolic 2N HCl. The stirred suspension turned homogeneous prior to the formation of a white precipitate. This precipitate was isolated and recrystallized from MeOH to provide, after two crops, 13.1 g (39.6 mmol) of pure monohydrochloride salt m.p. 258°-259° C. (dec.).

Free base: $^1$H NMR (200 MHz, DMSO-D$_6$) δ 12.00 (br s, 1H), 8.52 (br s, 1H), 8.42 (m, 1H), 7.65 (m, 1H), 7.30 (m, 2H), 4.55 (d, J=8 Hz, 2H), 2.15 (s, 3H);

IR (KBr) 3260, 3170 (NH), 3000, 2800 (CH), 1660 (C=O), 1600 (C=C, C=N) cm$^{-1}$;

UV (MeOH) λ 270.0 (ε9877), 221.5 (ε26,640);

mass spectrum m/e 296 (M$^+$, 35%), 294 (M$^+$, 36%), 215 (M$^+$—Br, 50%), 107 (C$_6$H$_7$N$_2$, 100%);

Anal. Calcd. for C$_{11}$H$_{11}$N$_4$BrO: C 44.76, H 3.76, N 18.98. Found: C 44.58, H 3.99, N 18.71.

HCl salt: $^1$H NMR (200 MHz, DMSO-D$_6$) δ 12.1 (br s, 1H), 8.78 (m, 2H), 8.40 (m, 1H), 7.95 (m, 1H), 7.42 (m, 1H, NH), 4.70 (d, J=8 Hz, 2H), 2.15 (s, 3H);

IR (KBr) 3370 (NH), 2500-3000 (CH), 1650 (C=O), 1610, 1585 (C=C, C=N) cm$^{-1}$;

UV (MeOH) λ 266.5 (ε10,540), 221.0 (ε30,620);

mass spectrum m/e 296 (M+—HCl, 49%), 294 (M+—HCl, 49%), 215 (M+—HCl—Br, 93%), 107 ($C_6H_7N_2$, 100%);

EXAMPLE 2

1,4-Dihydro-2,5-dimethyl-6-[[2-(1-methyl-1H-pyrrol-2-yl)ethyl]amino]-4-pyrimidinone

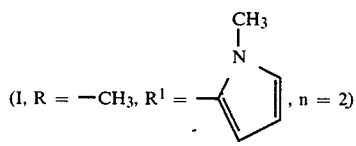

(Step a) Preparation of 2,5-Dimethyl-4,6-dihydroxypyrimidine

According to the procedure of D. J. Brown et al., *J. Chem. Soc.* 1964, 3204, a solution of 9.2 g (400 mmol) of sodium metal dissolved in 200 mL of methanol was treated first with 19.8 g. (210 mmol) of acetamidine hydrochloride and then with 34.4 mL (34.8 g, 200 mmol) of diethyl methyl malonate. The reaction mixture was heated to reflux for 4 hours, cooled to 23° C., and filtered. The filtrate was concentrated in vacuo. The residue from the filtrate and the isolated solids were combined and dissolved in water (300 mL). The aqueous solution was acidified with aqueous 3N HCl (133 mL). The fine white solid which precipitated from this solution was isolated by filtration and dried in vacuo to give 24.9 g (89%) of pure product, m.p. 300° C.

$^1$H NMR (60 MHz, TFAA) δ 2.88 (s, 3H), 2.2 (s, 3H);
IR (Nujol) 3550, 1620, 1270–1320, 1040 cm$^{-1}$;
mass spectrum m/e 140 (M+, 100%), 112 (M+—CO, 63%).

(Step b) Preparation of 4,6-Dichloro-2,5-dimethylpyrimidine

A suspension of 2,5-dimethyl-4,6-dihydroxypyrimidine (14 g, 100 mmols) in phosphorous oxychloride (45.9 g, 300 mmol, 20 mL) was heated to reflux for 3 hours. At the end of this time, the reaction mixture was poured into an ice/water slurry in which sodium hydroxide had been dissolved (44 g, 1.1 mmol). The mixture was stirred for 15 minutes and then extracted with methylene chloride. The combined organic extracts were dried, filtered, and concentrated in vacuo to provide a yellow oil which crystallized upon standing to afford yellow crystals (14.6 g) 82%, m.p. 46°–47° C.

$^1$H NMR (60 MHz, CDCl$_3$) δ 2.7 (s, 3H), 2.5 (s, 3H);
Ir (CHCl$_3$) 1550, 1500, 1025 cm$^{-1}$;
mass spectrum m/e 176 (M+85%), 141 (M+—Cl, 100%).

(Step c) Preparation of 2,5-Dimethyl-4-hydroxy-6-chloropyrimidine

To a solution of water (5.6 mL) in sulfuric acid (21 mL) at 20° C. was added the 4,6-dichloro-2,5-dimethylpyrimidine (9.3 g, 52.5 mmol). The reaction mixture was stirred for 2 hours at 23° C. and then poured onto ice to which sodium hydroxide (16 g, 400 mmol) had been added. When the ice melted, sodium chloride (60 g) was dissolved in the solution which was then extracted with ethyl acetate. The combined ethyl acetate extracts were dried, filtered, and concentrated in vacuo to afford 7.8 g (94%) of product as a fluffy white solid. The recrystallization of the product from ethanol provided an analytically pure sample, m.p. 224°–225° C.

$^1$H NMR (60 MHz, CDCl$_3$) δ 13.6 (br s, 1H), 2.5 (s, 3H), 2.15 (s, 3H);
IR (CHCl$_3$) 3000, 1660, 1600 cm$^{-1}$;
mass spectrum m/e 158 (M+, 100%), 129 (M+—HCO, 34%);
Anal. Calcd. for $C_6H_7ClN_2O$: C, 45.43; H, 4.42; N, 17.67. Found: C, 45.41 H, 4.52; N, 17.61.

(Step d) Preparation of 1,4-Dihydro-2,5-dimethyl-6-[[2-(1-methyl-1H-pyrrol-2-yl)ethyl]amino]-4-pyrimidone A stirred suspension of 2.00 g (12.9 mmol) of 2,5-dimethyl-4-hydroxy-6-chloropyrimidine and 6.5 mL (52 mmol, 4 equiv.) of 2-(2-aminoethyl)-1-methylpyrrole in 10 mL of DME was heated at 90° C. for 18 hours under a dry atmosphere. The reaction mixture was cooled to 23° C. and filtered. The isolated solids were rinsed with Et$_2$O, H$_2$O, and MeOH and then recrystallized from MeOH to afford 2.63 g 83% (10.7 mmol) of pure product, m.p. 246°–247° C. as a white powder.

$^1$H NMR (200 MHz, DMSO-D$_6$) δ 11.32 (br s, 1H, NH), 6.58 (t, J=2 Hz, 1H), 6.08 (t, J=7 Hz, 1H), 5.83 (t, J=3 Hz, 1H), 5.76 (m, 1H), 3.54 (s, 3H), 3.44 (m, 2H), 2.69 (t, J=8 Hz, 2H), 2.14 (s, 3H), 1.67 (s, 3H);
IR (KBr) 3400 (OH), 3039, 2600–3000 (CH), 1610 (C=C, C=N) cm$^{-1}$;
UV (MeOH) λ 272.5 (ε 11,810);
mass spectrum m/e 246 (M+, 24%), 107 ($C_7H_9N$, 100%);
Anal. Calcd. for $C_{13}H_{18}N_4O$: C 63.41, H 7.32, N 22.76. Found: C 63.11, H 7.15, N 22.62.

EXAMPLE 3

5-Chloro-2-methyl-6-[(3-pyridinylmethyl)amino]-4-pyrimidinol

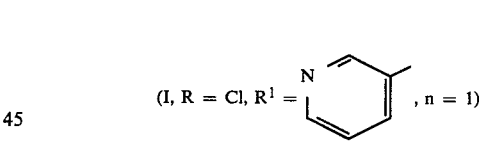

(Step a) Preparation of 2-Methy-4-hydroxy-5,6-dichloropyrimidine

To 21.7 g (110 mmol) of 2-methyl-4,5,6-trichloropyrimidine was added 150 mL of 3.6:1 concentrated H$_2$SO$_4$:H$_2$O solution. The mixture was stirred at 23° C. for 90 minutes during which time the suspended solids completely dissolved. The homogeneous solution was poured cautiously onto 35.2 g (88.0 mmol, 4 equiv.) of NaOH in ice. After the ice had melted (final volume 400 mL), the white precipitate was isolated by filtration, washed with water (3×50 mL), and recrystallized from MeOH to afford 18.5 g (103 mmol, 94%) of product, m.p. 252°–253° C.

$^1$H NMR (200 MHz, DMSO-D$_6$) δ 12.65 (br s, 1H, OH), 2.22 (s, 3H);
IR (KBr) 2700–3000 (CH), 1670, 1590 (C=C, C=N) cm$^{-1}$;
UV (MeOH) λ 284.5 (ε 6030);
mass spectrum m/e 180 (M+, 60%), 178 (M+, 100%).

(Step b) Preparation of
5-Chloro-2-methyl-6-[(3-pyridinylmethyl)amino]-4-pyrimidinol To a suspension of 2-methyl-4-hydroxy-5,6-dichloropyrimidine (5.37 g, 30 mmol) in DME (40 mL) was added 3-(aminomethyl)pyridine (9.1 mL, 9.5 g, 90 mmol). The reaction was heated to 65° C. for 11 hours, cooled to 23° C., diluted with diethyl ether and water, stirred a few minutes, and filtered. The isolated precipitate was washed with a few milliliters of water and partially dried to give crude product (5.0 g, 65%). The crude product was pooled with similarly prepared material and recrystallized from methanol to give pure white solid product (5.4 g) m.p. 270°–272° C.

$^1$H NMR (200 MHz, DMSO-D$_6$) δ 8.5 (m, 2H), 7.7 (m, 1H), 7.5 (t, 1H, NH), 7.3 (m, 1H), 4.6 (d, 2H), 2.2 (s, 3H);

IR (KBr) 3260, 2500–3000, 1660, 1600, 1500 cm$^{-1}$;
UV (MeOH) λ 270.0 (ε 10,650), 221.5 (ε 25,690);
mass spectrum m/e 250 (M+, 28%), 107 (C$_6$H$_7$N$_2$, 100%);

Anal. Calcd. for C$_{11}$H$_{11}$N$_4$O Cl: C, 52.69; H, 4.39; N, 22.35. Found: c, 52.56; H, 4.43; N, 22.23.

EXAMPLE 4

5-Chloro-2-methyl-6-[(2-phenylethyl)amino]-4-pyrimidinol (I, R=Cl, R$^1$=phenyl, n=2

A suspension of 2-methyl-4-hydroxy-5,6-dichloropyrimidine prepared in Example 3, (Step a) (2.69 g, 15 mmol) in DME was treated with phenylethylamine (5.6 mL, 5.45 g, 45 mmol). The reaction mixture was heated to reflux for 3 hours and then solvent was removed in vacuo. The residue was triturated with a small amount of water and isolated by filtration to give crude product (2.2 g). This crude material was recrystallized from methanol to give 2.0 g (51%) of pure white solid product, m.p. 230°–232° C.

$^1$H NMR (200 MHz, DMSO-D) δ 11.9 (s, 1H, OH), 7.25 (m, 5H, arom.), 6.8 (t, 1H, NH), 3.55 (m, 2H), 2.8 (t, 2H), 2.2 (s, 3H);

IR (KBr) 3410, 2100–2500, 1665, 1600, 1500 cm$^{-1}$;
UV (MeOH) λ 274.5 (ε 9781), 223.5 (ε 26,240);
mass spectrum m/e 263 (M+, 7%), 172 (M+—C$_7$H$_7$, 100%), 91 (C$_7$H$_7$, 23%);

Anal. Calcd. for C$_{12}$H$_{14}$N$_3$ClO: C, 59.20; H, 5.31; N, 15.94. Found: C, 59.17; H, 5.37; N, 15.99.

EXAMPLE 5

1,4-Dihydro-2,5-dimethyl-6-[(3-pyridinylmethyl)amino]-pyrimidine-4-one

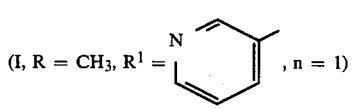

(I, R = CH$_3$, R$^1$ = [pyridine structure], n = 1)

To a suspension of 2,5-dimethyl-4-hydroxy-6-chloropyrimidine (1.59 g, 10 mmol) in 10 mL of THF was added 3.1 mL (3.24 g, 30 mmol) of 3-methylamino pyridine. The mixture was heated to reflux for 40 hours, cooled to 23° C., and filtered. The filtrate was triturated with water (20 mL) and refiltered. The isolated solid was recrystallized from a methanol-diethyl ether mixture to afford 1.7 g (55%) of pure product, m.p. 282°–284° C.

$^1$H NMR (200 MHz, DMSO-D$_6$) δ 11.75 (br s, 1H), 8.5 (m, 2H), 7.8 (m, 1H), 7.4 (m, 1H), 6.05 (t, 1H), 4.6 (d, 2H), 2.2 (s, 3H), 1.8 (s, 3H);

IR (KBr) 3320, 2200–3200, 1600 cm$^{-1}$;
UV (MeOH) λ 270 (ε 11,500), 220 (ε 38,2040);
mass spectrum m/e 230 (M+, 100%);

Anal. Calcd. for C$_{12}$H$_{14}$N$_4$O: C, 62.60; H, 6.08; N, 24.34. Found: C, 62.10; H, 5.95; N, 24.89.

EXAMPLE 6

5-Fluoro-1,4-dihydro-2-methyl-6-[(3-pyridinylmethyl)amino]-4-pyrimidinone

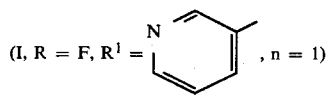

(I, R = F, R$^1$ = [pyridine structure], n = 1)

(Step a) Preparation of Diethyl fluoromalonate

According to the procedure of J. Chem. Soc. 1959, 3286, to a suspension of sodium hydride (2.4 g, 50 mmol, prewashed twice with hexanes) in 10 mL of THF was added dropwise 4.8 mL (5.3 g, 50 mL) of ethyl fluoroacetate. After the addition had been completed, a vigorous reaction was observed. The resulting mixture was stirred for 15 minutes, and then 4.8 mL (5.4 g, 50 mmol) of ethyl chloroformate in 5 mL of THF was added. This mixture was heated at reflux for 18 hours, cooled to 23° C., and diluted cautiously with water. The mixture was extracted with ethyl acetate. The combined organic layers were extracted with saturated saline, dried (MgSO$_4$), and concentrated in vacuo. The residue (5.7 g) was purified by HPLC to give pure product (1.95 g, 22%) as a yellow oil.

$^1$H NMR (60 MHz, CDCl$_3$) δ 5.31 (t, 1H), 4.40 (q, 4H), 1.35 (t, 6H);
IR (CHCl$_3$) 1750 cm$^{-1}$.

(Step b) Preparation of 2-Methyl-4,6 dihydroxy-5-fluoropyrimidine

According to the procedure of J. Chem. Soc. 1959, 3286, a solution of 0.92 g (40 mmol) of sodium metal dissolved in 20 mL of methaol was treated with 2.08 g (22 mmol) of acetamidine hydrochloride. After 5 minutes, to this stirred mixture was added 3.6 g (20 mmol) of diethyl fluoromalonate. The reaction mixture was heated to reflux for 18 hours, cooled to 23° C., and then concentrated in vacuo. The residue was dissolved in water, neutralized with aqueous 3N HCl (6 mL), and chilled. A precipitate which formed was isolated by filtration and triturated with a 1:1 mixture of diethyl ether/ethyl acetate. The resulting crude product (1.36 g, 47%) was used without further purification.

$^1$H NMR (60 MHz, DMSO-D$_6$) δ 6.3 (br s, 2H), 2.32 (s, 3H);
IR (Nujol) 3400–3600, 1690, 1650 cm$^{-1}$.

(Step c) Preparation of
2-Methyl-4,6-dichloro-5-fluoropyrimidine

A suspension of 1.44 g (10 mmol) of 2-methyl-4,6-dihydroxy-5-fluoropyrimidine in 7.5 mL (12 g, 80 mmol) of phosphorus oxychloride was heated to reflux for 4 hours. The mixture was cooled to 23° C., and poured into an ice/water slurry in which sodium hydroxide (15.0 g) had been dissolved. The mixture was stirred for 20 minutes and then extracted with chloroform. The combined organic extracts were dried (MgSO$_4$), filtered, and concentrated in vacuo to provide product (0.78 g, 43%), m.p. 49°–50° C. This crude product was used in subsequent reactions without further purification.

$^1$H NMR (60 MHz, CDCl$_3$) δ 2.7 (s, 3H);

IR (CHCl$_3$) 1520, 1415 cm$^{-1}$;

mass spectrum m/e 180 (M+, 29%), 145 (M+-Cl, 68%).

(Step d) Preparation of 2-Methyl-4-hydroxy-5-fluoro-6-chloropyrimidine

To a mixture of water (3 mL) and concentrated sulfuric acid (7 mL) was added 1.81 g (10 mmol) of 2-methyl-4,6-dichloro-5-fluoropyrimidine. The reaction mixture was stirred for 3 hours and then poured onto ice. The mixture was saturated with sodium chloride and extracted with ethyl acetate. The organic extracts were combined, dried (MgSO$_4$), filtered, and concentrated in vacuo to give crude product (1.4 g, 86%), m.p. 214°–216° C. This product was used in subsequent reactions without further purification.

$^1$H NMR (60 MHz, CDCl$_3$) δ 2.42 (s, 3H);

IR (Nujol) 1650, 1585, 1450 cm$^{-1}$.

(Step e) 5-Fluoro-1,4-dihydro-2-methyl-6-[(3-pyridinylmethyl)amino]-4-pyrimidone To a suspension of 0.89 g (5.5 mmol) of 2-methyl-4-hydroxy-5-fluoro-6-chloropyrimidine in 7 mL THF was added 2.24 mL (2.38 g, 22 mmol) of 3-(methylamino) pyridine. The reaction mixture was heated to reflux for 40 hours, cooled to 23° C., diluted with diethyl ether (15 mL), and filtered. The isolated solid was triturated with water (10 mL) and refiltered. The isolated crude product (1.12 g) was combined with material similarly prepared (total 1.29 g) and recrystallized from methanol to give pure product (1.01 g, 65%), m.p. 254°–256° C.

$^1$H NMR (200 MHz, DMSO-D$_6$) δ 8.5 (m, 2H) 7.7 (m, 1H), 7.5 (t, 1H), 7.35 (m, 1H), 4.55 (d, 2H), 2.15 (s, 3H);

IR (KBr) 3260, 3200, 2700–3100, 1660–1700, 1600–1630, 1450 cm$^{-1}$;

UV (MeOH) λ 270.5 (ε 13,790), 218.5 (ε 27,480) nm; mass spectrum m/e 234 (M+, 100%);

Anal. Calcd. for C$_{11}$H$_{11}$N$_4$FO: C, 56.41; H, 4.70; N, 23.93. Found: C, 55.90; H, 5.01; N, 23.93.

EXAMPLE 7

2-Methyl-5-(1-methylethyl)-6-[(3-pyridinylmethyl)amino]-4-pyrimidinol

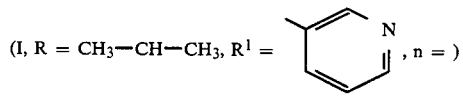

(Step a) Preparation of 2-Methyl-5-(1-methylethyl)-6-chloro-4-pyrimidinol

A homogeneous solution of 47.0 g (229 mmol) of 2-methyl-4,6-dichloro-5-(1-methylethyl)-pyrimidine in 200 mL of a 3.6:1 concentrated H$_2$SO$_4$:H$_2$O solution was stirred at 23° C. for 2 hours and then cautiously poured onto an ice-water mixture containing 82 g (1.5 mmol, 6 equiv.) of KOH. After the ice had melted, the aqueous layer was extracted with chloroform (5×200 ml). The combined organic layers were dried (MgSO$_4$), filtered, and concentrated in vacuo to afford 36.2 g (193 mmol, 84%) of white solid product. Analytically pure product was obtained by recrystallization from ethanol, m.p. 157°–158° C.

$^1$H NMR (200 MHz, CDCl$_3$) δ 3.33 (m, 1H), 2.43 (s, 3H), 1.31 (d, J=7.0 Hz, 6H);

IR (CHCl$_3$) 2760–3000 (CH), 1650 (C=O), 1600 (C=C, C=N) cm$^{-1}$;

UV (MeOH) λ 278.0 (ε 6094), 231.0 (ε 5420);

mass spectrum m/e 186 (M+, 27%), 171 (M+—Me, 100%);

Anal. Calcd. for C$_8$H$_{11}$N$_2$ClO: C 51.48, H 5.94, N 15.01. Found: C 51.37, H 5.87, N 14.84.

(Step b) Preparation of 2-Methyl-5-(1-methylethyl)-6-[(3-pyridinylmethyl)amino]-4-pyrimidinol To a suspension of 3.92 g (21 mmol) of 2-methyl-5-(1-methylethyl)-6-chloro-4-pyrimidinol in 12 mL of THF was added 6.4 mL (63 mmol) of 3-(methylamino)pyridine. The reaction mixture was heated to reflux for 48 hours and then treated with an additional 4.3 mL (42 mmol) of 3-(methylamino)pyridine. The reaction mixture was heated for an additional 20 hours at reflux temperature, cooled to 23° C., diluted with diethyl ether (25 mL), and filtered. The isolated solid was triturated with water (25 mL) to give 4.3 g of crude product. This product was combined with similarly prepared material (total 4.6 g) and recrystallized from a mixture of methanol/diethyl ether to give pure product (3.58 g, 58%), m.p. 214°–216° C.

$^1$H NMR (200 MHz, DMSO-D$_6$) δ 8.5 (m, 2H), 7.7 (m, 1H), 7.3 (m, 1H), 4.5 (s, 2H, NH, OH), 3.3 (d, 2H), 2.9 (m, 1H), 2.0 (s, 3H), 1.2 (d, 6H);

IR (KBr) 3280, 1620 cm$^{-1}$;

UV (MeOH) λ 270 (ε 9500);

mass spectrum m/e 258 (M+, 46%); 243 (M+—Me, 68%);

Anal. Calcd. for C$_{14}$H$_{18}$N$_4$O: C, 65.12; H, 6.98; N, 21.71. Found: C, 64.83; H, 7.23; N, 21.75.

EXAMPLE 8

2,5-Dimethyl-6-[(2-(4-pyridinyl)ethyl)amino]-4-pyrimidinol

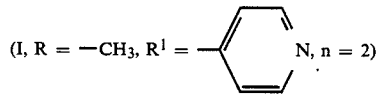

A suspension of 2.38 g (15 mmol) of 2,5-dimethyl-6-chloropyrimidinol in 10 mL of THF was treated with 9.0 mL (9.2 g, 75 mmol) of 2-(4-pyridinylethylamine. The reaction mixture was heated to reflux for 95 hours, cooled to 23° C., diluted with diethyl ether, and filtered. The isolated solid was triturated with water (25 mL) and then dried to give 2.23 g (34%) of crude product, m.p. 250°–252° C. This crude product was combined with material similarly prepared (total 2.76 g) and recrystallized from methanol/diethyl ether to give pure product (2.4 g).

$^1$H NMR (200 MHz, DMSO-D$_6$) δ 8.44 (q, 2H), 7.21 (q, 2H), 3.54 (m, 2H), 3.32 (br s, 2H, NH, OH), 2.81 (t, 2H), 2.14 (s, 3H), 1.65 (s, 3H);

IR (KBr) 3270, 2600–3000, 1580–1640, 1470 cm$^{-1}$;

UV (MeOH) λ 271.5 (ε 11,660);

mass spectrum m/e 244 (M+, 23%) 93 (C6H7N+, 100%);

Anal. Calcd. for C13H16N4O: C, 63,93; H, 6.56; N, 22.95. Found: C, 63.99; H, 6.78; N, 23.07.

EXAMPLE 9

5-Bromo-2-methyl-6-[(2-phenylethyl)amino]-4-pyrimidinol (I, R=Br, R$^1$=phenyl, n=2)

To a suspension of 3.35 g (15 mmol) of 2-methyl-4-hydroxy-5-bromo-6-chloropyrimidine (Example I, Step b) in 20 mL of DME was added 9.4 mL (9.1 g, 75 mmol) of 2-phenyl ethylamine. The reaction mixture was heated to reflux for one hour and then concentrated in vacuo. The residue was triturated with water (40 mL) and then dried to give 3.65 g of crude product. This crude material was combined with similarly prepared material (total 4.0 g) and recrystallized from methanol/chloroform to give pure white solid product (3.70 g, 67%), m.p. 237°–238° C.

$^1$H NMR (200 MHz, DMSO-D$_6$) δ 7.2–7.4 (m, 4H), 6.6 (t, 1H, NH), 3.55 (m, 2H), 2.8 (m, 2H), 2.2 (s, 3H);

IR (KBr) 3400, 2500–3000, 1660, 1600, 1500 cm$^{-1}$;

UV (MeOHJ) λ 277.5 (ε 9280);

mass spectrum m/e 309 (M+, 11%), 307 (M+, 11%), 218 (M+—C7H7, 100%), 216 (M+—C7H7, 97%), 91 (C7H7, 10%);

Anal. Calcd. for C13H14N3BrO: C, 50.65; H, 4.55; N, 13.64. Found: C, 50.57; H, 4.74; N, 13.48.

EXAMPLE 10

5-Bromo-2-methyl-6-[[2-(4-pyridinyl)ethyl]amino]-4-pyrimidinol

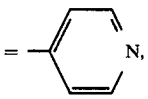

(I, R = Br, R$^1$ = , n = 2)

To a suspension of 2-methyl-5-bromo-6-chloropyrimidinol (2.24 g, 10 mmol) in 10 mL of dimethoxyethane was added 2-(4-pyridinyl)ethylamine (6.0 mL, 6.1 g, 50 mmol). The mixture was heated to reflux for 2 hours, cooled to 23° C., and then concentrated in vacuo. The residue was triturated with a water/diethyl ether mixture and then dried to afford 2.33 g (75%) of crude product. This crude material was combined with similarly prepared material (total 3.0 g) and recrystallized from a methanol/chloroform mixture to give pure white crystalline product (2.57 g), m.p. 245°–246° C.

$^1$H NMR (200 MHz, DMSO-D$_6$) δ 11.9 (br s, 1H, NH), 8.41 (d, 2H), 7.22 (d, 2H), 3.62 (q, 2H), 2.81 (t, 2H), 2.19 (s, 3H);

IR (KBr) 3215, 3125, 1590–1650 cm$^{-1}$;

UV (MeOH) λ 278 (ε 9160), 264 (ε 8640);

mass spectrum m/e 310 (M+, 6%), 308 (M+, 7%);

Anal. Calcd. for C12H13N4BrO: C, 46.60; H, 4.21; N, 18.12. Found: C, 46.58; H, 4.32; N, 17.81.

EXAMPLE 11

6-[(2-Furanylmethyl)amino]-2,5-dimethyl-4-pyrimidinol

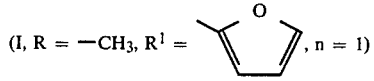

(I, R = —CH$_3$, R$^1$ = , n = 1)

A stirred solution of 2.27 g (14.3 mmol) of 2,5-dimethyl-4-hydroxy-6-chloropyrimidine in 5.05 mL (57.2 mmol, 5.55 g, 4 equiv.) of furfurylamine under nitrogen was heated at 120° C. for 23 hours and then cooled to 23° C. The mixture was diluted with 40 mL of water and filtered. The isolated precipitate was recrystallized twice from EtOAc to afford 1.34 g (6.11 mmol, 43%) of pure white crystalline product, m.p. 194°–5° C.

$^1$H NMR (200 MHz, DMSO-D$_6$) δ 11.56 (br s, 1H, OH), 7.52 (br s, 1H), 6.57 (t, J=4.1 Hz, 1H, NH), 6.35 (dd, J=3.2, 1.9 Hz, 1H), 6.5 (d, J=3.2 Hz, 1H), 4.52 (d, J=4.1 Hz, 2H), 2.14 (s, 3H), 1.70 (s, 3H);

IR (KBr) 3320 (OH, NH), 2700–2900 (CH), 1610 (C=C, C=N) cm$^{-1}$;

UV (MeOH) λ 272.5 (ε 10,700);

mass spectrum m/e 219 (M+, 93%), 81 (C5H5O, 100%);

Anal. Calcd. for C11H13N3O2: C 60.26, H 5.98, N 19.17. Found: C 60.24, H 6.04, N 19.46.

EXAMPLE 12

6-(Ethylamino)-2,5-dimethyl-4-pyrimidinol

A stirred mixture of 2.69 g (17.0 mmol) of 6-chloro-2,5-dimethy-4-pyrimidinol and 5.47 mL (85.0 mmol, 3.83 g, 5 equiv.) of ethylamine as a 70% w/w aqueous solution in a sealed 40 mL tube was heated at 90° C. for 1½ days and then cooled to 23° C. The white crystals which formed were recrystallized from MeOH and isolated by filtration to afford 1.14 g (6.83 mmol, 40%) of pure product. The filtrate was purified by flash chromatography (silica gel, 36 mm column, 5% MeOH in EtOAc as eluant) to give 830 mg (31%) of recovered starting material and an additional 590 mg (20%) of pure product. Washing with water and then diethyl ether before in vacuo drying provided analytically pure product as a white powder, m.p. 206°–207° C.

$^1$H NMR (60 MHz, CDCl$_3$) δ 4.3 (s, 1H, NH), 3.5 (q, J=7 Hz, 2H), 2.4 (s, 3H), 1.85 (s, 3H), 1.2 (t, J=7 Hz, 3H);

IR (KBr) 3370 (NH), 3290 (NH), 2600–3000 (CH), 1575–1650 (C=O, C=N, C=C) cm$^{-1}$;

UV (MeOH) λ 270.5 (ε 11,080);

mass spectrum m/e 167 (M+, 100%), 152 (M+—CH3, 55%), 139 (M+—C2H4, 31%), 111 (M+—C2H4, 31%), 138 (M+—C2H5, 19%);

Anal. Calcd. for C8H13N3O: C, 57.46; H, 7.84; N, 25.13. Found: C, 57.39; H, 7.71; N, 25.11.

EXAMPLE 13

6-[(Cyclopropylmethyl)amino]-2,5-dimethyl-4-pyrimidinol

To 3.92 g (36.3 mmol, 4 equiv.) of (aminomethyl)cyclopropane hydrochloride was added 2.5 g (44.6 mmol) of potassium hydroxide dissolved in 10 mL of water. The resulting slurry was thoroughly mixed and then dried with 1.0 g of KOH. The free amine was filtered through anhydrous K$_2$CO$_3$ with dry THF rinses (3×2 mL) into 1.44 g (9.08 mmol) of 6-chloro-2,5-dimethyl-4-pyrimidinol. The stirred clear solution was heated at 80° C. for 3½ days in a sealed 40 mL tube. The cooled, 23° C., mixture was purified by flash chromatography (silica gel, 41 mm column, 5% MeOH in EtOAc as eluant) to afford 1.42 g (7.36 mmol, 81%) of pure product m.p. 227°-228° C.

$^1$H NMR (60 MHz, DMSO-D$_6$) δ 11.7 (brs, 1H, OH), 6.28 (t, J=6 Hz, 1H, NH), 3.22 (t, J=6 Hz, 2H), 2.2 (s, 3H), 1.8 (s, 3H), 1.0 (m, 1H), 0.35 (m, 4H);

IR (KBr) 3400 (NH, OH), 2600-3000 (CH), 1600-1650 (C=C) cm$^{-1}$;

UV (MeOH) λ 271 (ε 11,060);

mass spectrum m/e 193 (M$^+$, 60%), 178 (M$^+$—CH$_3$, 48%), 164 (M$^+$—C$_2$H$_5$, 100%);

Anal. Calcd. for C$_{10}$H$_{15}$N$_3$O: C, 62.15; H, 7.82; N, 21.74. Found: C, 61.88; H, 7.77; N, 21.40.

EXAMPLE 14

6-(Ethylamino)-2-methyl-5-(1-methylethyl)-4-pyrimidinol

A mixture of 3.00 g (16.1 mmol) of 6-Chloro-2-methyl-5-(1-methylethyl)-4-pyrimidinol and 10.4 mL (7.24 g, 161 mmol, 10 equiv.) of ethylamine as a 70% w/w aqueous solution was sealed in a glass flask, heated at 90° C. for 5 days, and then cooled to 23° C. The mixture was concentrated in vacuo and purified by flash chromatography (silica gel, 50 mm column, 500 mL 4:1 EtOAc:hexane then EtOAc as eluent, mixed fractions rechromatographed) to provide 1.32 g (7.01 mmol, 44%) of recovered starting material and, after recrystallization from EtOAc, 1.70 g (8.70 mmol, 54%) of analytically pure product as a dense white crystalline solid, m.p. 179.5°-180° C.

$^1$H NMR (200 MHz, CDCl$_3$) δ 13.10 (br s, 1H), 4.42 (br s, 1H), 3.49 (m, 2H), 2.99 (m, 1H), 2.33 (s, 3H), 1.29 (d, J=7 Hz, 6H), 1.20 (t, J=7 Hz, 3H);

IR (KBr) 3420 (NH), 2600-3000 (CH), 1635, 1610, 1585 (C=C, C=N) cm$^{-1}$;

UV (MeOH) λ 272.5 (ε 10,1400), 222.5 (ε 188,700);

mass spectrum m/e 195 (M$^+$, 35%), 180 (M$^+$—Me, 100%);

Anal. Calcd. for C$_{10}$H$_{17}$N$_3$O: C, 61.51; H, 8.78; N, 21.52. Found: C, 61.79; H, 8.93; N, 21.62.

EXAMPLE 15

5-Bromo-1,4-dihydro-6-(ethylamino)-2-methyl-4-pyrimidinone

A stirred clean, 23° C., homogeneous solution of 4.10 g (26.8 mmol) of 6-ethylamino-2-methylpyrimidin-4-ol in 50 mL of chloroform and 15 mL of glacial acetic acid was treated dropwise with 1.80 mL (5.56 g, 34.8 mmol, 1.3 equiv.) of bromine. The reaction mixture was concentrated in vacuo after 63 hours of stirring. The residue was heated to reflux for 15 minutes in 100 mL of water, cooled to 23° C., isolated by filtration and recrystallized from diethyl ether:methylene chloride mixtures to provide a total of 4.12 g (66%) of pure white crystalline powder product, m.p. 201.5°-202.0° C.

$^1$H NMR (200 MHz, DMSO-D$_6$) δ11.95 (br s, 1H, Ch) 6.62 (t, J=5 Hz, 1H, NH), 3.38 (q, J=6 Hz, 2H), 2.18 (s, 3H), 1.08 (t, J=6 Hz, 3H);

IR (KBr) 3420, 2600-3000, 1640, 1605, 1580 cm$^{-1}$;

UV (MeOH) λ275.5 (ε 8340);

mass spectrum m/e 233 (M$^+$, 81%), 231 (M$^+$, 80%), 218 (M$^+$—CH$_3$, 98%), 216 (M$^+$—CH$_3$, 95%), 205 (M$^+$—C$_2$H$_5$, 38%), 203 (M$^+$—C$_2$H$_5$, 41%);

Anal. Calcd. for C$_7$H$_{10}$BrN$_3$O: C, 36.23; H, 4.34; N, 18.11. Found: C, 36.03; H, 4.37; N, 17.81.

EXAMPLE 16

5-Bromo-6-[(2-hydroxyethyl)amino]-2-methyl-4-pyrimidinol

A stirred, 23° C., suspension of 8.99 g (40.4 mmol) of 2-methyl-5-bromo-6-chloro-4-pyrimidinol in 45 mL of DME was treated over the course of 30 minutes with a solution of 9.76 mL (9.88 g, 162 mmol, 4 equiv.) of ethanolamine in 45 mL of DME. The stirred mixture was heated to 95° C. for 18 hours, cooled to 23° C., and concentrated in vacuo. The semi-solid residue was recrystallized from methanol to afford 9.23 g (37.2 mmol, 92%) of solid white product, m.p. 230°-231° C. (dec.).

$^1$H NMR (200 MHz, DMSO-D$_6$) δ 6.40 (t, J=5 Hz, 1H, NH), 4.73 (t, J=5 Hz, 1H, OH), 3.4 (m, 4H), 2.15 (s, 3H);

IR (KBr) 3370, 3310, 2700-3100, 1615, 1580 cm$^{-1}$;

UV (MeOH) λ 277.5 (ε 7850);

mass spectrum m/e 249 (M$^+$, 26%), 247 (M$^+$, 23%), 218 (M$^+$—CH$_3$O, 96%), 216 (M$^+$—CH$_3$O, 100%);

Anal. Calcd. for C$_7$H$_{10}$BrN$_3$O$_2$: C, 33.89; H, 4.06; N, 16.94. Found: C, 34.08; H, 4.01; N, 16.67.

EXAMPLE 17

6-[(Cyclopropylmethyl)amino]-2-methyl-5-(1-methylethyl)-4-pyrimidinol

A slurry of 7.24 g (67.0 mmol, 5 equiv.) of (aminomethyl)cyclopropane hydrochloride in 2.5 mL of water and 3.75 g (67.0 mmol) of potassium hydroxide (KOH) was dried with 8 g of KOH and rinsed with THF (5×3 mL). The THF rinses were sequentially filtered through a plug of anhydrous potassium carbonate (K$_2$CO$_3$) into a flask containing 2.50 g (13.4 mmol) of 2-methyl-5-(1-methylethyl)-6-chloro-4-pyrimidinol.

The flask was sealed and the stirred reaction mixture was heated at 100° C. for 65 hours. The clear yellow mixture was concentrated in vacuo and the residue was purified by flash chromatography (silica gel, 50 mm column, EtOAc as eluant; mixed fractions rechromatographed) to afford 850 mg (4.55 mmol, 34%) of recovered starting material and, after recrystallization from EtOAc, 1.51 g (6.82 mmol, 51%) of pure product, m.p. 167°-168° C.

$^1$H NMR (200 MHz, CDCl$_3$) δ 13.2 (br s, 1H), 4.68 (br s, 1H), 3.31 (dd, J=7.2, 5.3 Hz, 2H), 3.04 (m, 1H), 2.31 (s, 3H), 1.29 (d, J=7.2 Hz, 6H), 1.08 (m, 1H), 0.54 (m, 2H), 0.25 (m, 2H);

IR (KBr) 3485 (NH), 2800-3000 (CH), 1620, 1575 (C=C, C=N) cm$^{-1}$;

UV (MeOH) λ 273.0 (ε 10,210), 222.0 (ε 21,440);

mass spectrum m/e 221 (M$^+$, 100%), 192 (M$^+$—C$_2$H$_5$, 73%);

Anal. Calcd. for C$_{12}$H$_{19}$N$_3$O: C, 65.13; H, 8.65; N, 18.99. Found: C, 64.91; H, 8.52; N, 18.88.

EXAMPLE 18

Test for Cardiotonic Activity in Isolated Cat Papillary Muscle

A cat of either sex was anesthetized with Na pentobarbital, 25-30 mg/kg i.v. The heart was rapidly removed and placed in cool Tyrode's solution which had been equilibrated with 95% O$_2$-5% CO$_2$. The right ventricle was opened by cutting down the sides and around the apex so that the free wall could be folded back on the atriventricular groove. Usually at least three suitably-sized papillary muscles were found (1 mm or less in thickness). Threads were tied around the chordae tendonae and the base of the muscle just above its point of insertion into the ventricular wall. The chordae were cut, and the muscle was removed along with a small button of ventricular wall. If a sufficient number of papillary muscles were not present, trabeculae carnae could also be used. The best ones were usually found inserting just under the valve.

The preparations were mounted in tissue baths containing Tyrode's solution at 37° C. bubbled with 95% $O_2$–5% $CO_2$. One thread was affixed to a tissue holder incorporating a pair of platinum electrodes and the other thread was attached to a force displacement transducer. Initial tension placed on the preparation was 0.2 g (less for very small muscles). The preparations were stimulated with square-wave pulses, 2–4 msec. in duration and 10% above threshold voltage, at a rate of 0.5 Hz. The muscles were then gently and gradually stretched to their optimum force-length relation (at which twitch tension was maximal—further stretching did not result in any further increase in the overall magnitude of the twitch). The preparations were then allowed to equilibrate for one hour with frequent changes of the bathing fluid (10–15 min. intervals). The test compound was added to the bath in 0.1 mL of vehicle and incubated with the preparation for 15 min. or until peak effect was attained.

Using this method, the following representative compounds of formula I were effective for increasing the force of contraction of the papillary muscle.

TABLE 1

| Test Results of Cardiotonic Activity in Isolated Cat Papillary Muscle | |
|---|---|
| Compound of Example # | $EC_{50}$ |
| 1 | $2.5 \times 10^{-6}$ M |
| 2 | $2.9 \times 10^{-6}$ M |
| 3 | $1.0 \times 10^{-6}$ M |
| 4 | $1.5 \times 10^{-6}$ M |
| 5 | $1.1 \times 10^{-5}$ M |
| 6 | (69% increase at $10^{-4}$ M) |
| 7 | $7.4 \times 10^{-6}$ M |
| 8 | (52% increase at $10^{-4}$) |
| 9 | $1.3 \times 10^{-5}$ |
| 10 | $2.5 \times 10^{-4}$ |
| 11 | $1 \times 10^{-5}$ M |
| 12 | $5 \times 10^{-6}$ M |
| 13 | $3.7 \times 10^{-6}$ M |
| 14 | (86% increase at $10^{-4}$ M) |
| 15 | $2.8 \times 10^{-6}$ M |
| 16 | $8.2 \times 10^{-6}$ M |
| 17 | (185% increase at $10^{-4}$ M) |

EXAMPLE 19

Pentobarbital-induced Cardiac Failure in the Dog

A dog of either sex was anesthetized with Na pentobarbital, 30–35 mg/kg i.v. The trachea was intubated and the animal was respired at a rate of 20 breaths/min (stroke volume=15 cc/kg). Both femoral veins were cannulated. One cannula was used for infusion of pentobarbital to induce and maintain failure, the other for injection of test compounds. A cannual was inserted into the aorta via a femoral artery and the cannula was attached to a blood pressure transducer for measurement of systolic, diastolic and mean aortic blood pressure. A Millar pressure-tip catheter was inserted into the other femoral artery and advanced into the left ventricle to record intraventricular pressure and dP/dt. Subdermal needle electrodes were used to record a lead II electrocardiogram and heart rate.

Following a stabilization period of at least 30 min, experimental failure was induced by the i.v. infusion of Na pentobarbital, 0.75 mg/kg/min in 0.2 mL of saline/min, until a 40–50% decrease in peak positive dP/dt was obtained. The failure state was maintained at this level throughout the experiment by continuous infusion of Na pentobarbital, 0.11–0.15 mg/kg/min. Once the maintenance infusion was started, at least 15 min were allowed to elapse before test drugs were administered.

Test compounds were prepared in N saline. Increasingly higher doses were given i.v. at 30 min-1 hr intervals in order to determine a therapeutic (50% increase in dP/dt) to toxic (appearance of arrhythmias) ratio where possible.

Using this method, the following representative compounds of formula I were effective for increasing the cardiac contractility of the heart (the amount of test compound in mg per kg of body weight administered i.v. to give a 50% increase in dP/dt.

TABLE 2

| Pentobarbital-Induced Cardiac Failure in the Dog | |
|---|---|
| Compound of Example # | $ED_{50}$ mg/kg i.v. |
| 1 | 0.012 |
| 2 | — |
| 3 | 0.02 |
| 4 | 0.04 |
| 5 | 0.05 |
| 6 | — |
| 7 | 0.13 |
| 8 | — |
| 9 | 0.03 |
| 10 | — |
| 11 | — |
| 12 | 0.04 |
| 13 | 0.05 |
| 14 | 0.04 |
| 15 | 0.01 |
| 16 | — |
| 17 | 0.50 |

We claim:

1. A compound of the formula (I)

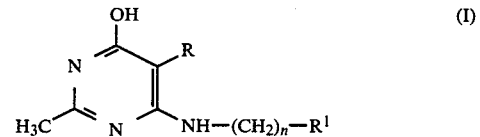

wherein R is halogen or lower alkyl having 1 to 3 carbon atoms; $R^1$ is hydrogen, hydroxy, cyclopropyl, pyridinyl, 1-methyl-1H-pyrrol-2-yl, 2-furanyl, phenyl; and n is an integer from 1 to 3, and the pharmaceutically acceptable addition salts thereof.

2. A compound according to claim 1 wherein R is halogen, methyl, isopropyl; $R^1$ is hydrogen, hydroxy, cyclopropyl, 3- and 4-pyridinyl, 1-methyl-1H-pyrrol-2-yl, 2-furanyl, and phenyl; and n is an integer from 1 to 3, and the pharmaceutically acceptable addition salts thereof.

3. A compound according to claim 2 wherein R is fluorine, chlorine, bromine, methyl, isopropyl, $R^1$ is hydrogen, hydroxy, cyclopropyl, 3- and 4-pyridinyl, 1-methyl-1H-pyrrol-2-yl, 2-furanyl, phenyl; and n is an integer from 1 to 3 and the pharmaceutically acceptable addition salts thereof.

4. The compound according to claim 1 designated 5-bromo-2-methyl-6-[(3-pyridinylmethyl)amino]-4-pyrimidinol.

5. The compound according to claim 1 designated 1,4-dihydro-2,5-dimethyl-6-[[2-(1-methyl-1H-pyrrol-2-yl)ethyl]amino]-4-pyrimidinone.

6. The compound according to claim 1 designated 5-chloro-2-methyl-6-[(3-pyridinylmethyl)amino]-4-pyrimidinol.

7. The compound according to claim 1 designated 5-chloro-2-methyl-6-[(2-phenylethyl)amino]-4-pyrimidinol.

8. The compound according to claim 1 designated 1,4-dihydro-2,5-dimethyl-6-[(3-pyridinylmethyl)amino]-pyrimidin-4-one.

9. The compound according to claim 1 designated 5-fluoro-1,4-dihydro-2-methyl-6-[(3-pyridinylmethyl)amino]-4-pyrimidinone.

10. The compound according to claim 1 designated 2-methyl-5-(1-methylethyl)-6-[(3-pyridinylmethyl)amino]-4-pyrimidinol.

11. The compound according to claim 1 designated 2,5-dimethyl-6-[(2-(4-pyridinyl)ethyl)amino]-4-pyrimidinol.

12. The compound according to claim 1 designated 5-bromo-2-methyl-6-[(2-phenylethyl)amino]-4-pyrimidinol.

13. The compound according to claim 1 designated 5-bromo-2-methyl-6-[[2-(4-pyridinyl)ethyl]amino]-4-pyrimidinol.

14. The compound according to claim 1 designated 6-[(2-furanylmethyl)amino]-2,5-dimethyl-4-pyrimidinol.

15. The compound according to claim 1 designated 5-bromo-1,4-dihydro-6-(ethylamino)-2-methyl-4-pyrimidinone.

16. The compound according to claim 1 designated 6-(ethylamino)-2,5-dimethyl-4-pyrimidinol.

17. The compound according to claim 1 designated 6-[(cyclopropylmethyl)amino]-2,5-dimethyl-4-pyrimidinol.

18. The compound according to claim 1 designated 5-bromo-6-[(2-hydroxyethyl)amino]-2-methyl-4-pyrimidinol.

19. The compound according to claim 1 designated 6-(ethylamino)-2-methyl-5-(1-methylethyl)-4-pyrimidinol.

20. A cardiotonic pharmaceutical composition, useful for increasing cardiac contractility in a mammal, which comprises an effective amount of a compound of claim 1 and a pharmaceutically acceptable carrier.

21. A cardiotonic pharmaceutical composition, which comprises a compound of claim 1 and an agent commonly used in treatment of congestive heart failure.

22. The cardiotonic pharmaceutical composition of claim 21 wherein said agent is selected from isosorbide dinitrate, captopril, nifedipine, hydralazine, prazosin, hydrochlorothiazide, furosemide, spironolactone, digitalis and dobutamine.

23. A method for increasing cardiac contractility in a mammal which comprises administering to the mammal an effective cardiotonic amount of a compound of formula I or a therapeutically acceptable addition salt thereof.

* * * * *